(12) United States Patent
Kato et al.

(10) Patent No.: US 12,138,663 B2
(45) Date of Patent: Nov. 12, 2024

(54) SORTING APPARATUS FOR SORTING OBJECTS AND MEASUREMENT APPARATUS

(71) Applicant: CANON KABUSHIKI KAISHA, Tokyo (JP)

(72) Inventors: Shigeki Kato, Tochigi (JP); Takuya Shimada, Tochigi (JP); Shinzo Uchiyama, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 18/309,502

(22) Filed: Apr. 28, 2023

(65) Prior Publication Data

US 2023/0364652 A1 Nov. 16, 2023

(30) Foreign Application Priority Data

May 12, 2022 (JP) ................................. 2022-078799

(51) Int. Cl.
| | |
|---|---|
| *G01N 21/85* | (2006.01) |
| *B07C 5/00* | (2006.01) |
| *B07C 5/10* | (2006.01) |
| *B07C 5/342* | (2006.01) |
| *G01N 21/25* | (2006.01) |
| *G01N 33/44* | (2006.01) |

(52) U.S. Cl.
CPC .............. *B07C 5/3422* (2013.01); *B07C 5/10* (2013.01); *G01N 21/255* (2013.01); *G01N 33/44* (2013.01)

(58) Field of Classification Search
CPC ......... B07C 5/3422; B07C 5/10; B07C 5/342; B07C 5/368; G01N 21/255; G01N 33/44; G01N 21/85; G01N 21/65; G01J 3/44

USPC ......................................................... 209/552
See application file for complete search history.

(56) References Cited

U.S. PATENT DOCUMENTS 5,471,311 A * 11/1995 van den Bergh ..... B07C 5/3416
356/407
5,862,919 A * 1/1999 Eason ....................... B07C 5/00
209/939

(Continued)

FOREIGN PATENT DOCUMENTS

CN       107505285 A  * 12/2017  ........... B07C 5/3422
DE     19816881 A1  * 10/1999  ........... B07C 5/3425

(Continued)

OTHER PUBLICATIONS

Nanoscale Three-dimensional Single Particle Tracking, 2011, vol. 3, 4532-4541 (Year: 2011).*

(Continued)

*Primary Examiner* — Gene O Crawford
*Assistant Examiner* — Muhammad Awais
(74) *Attorney, Agent, or Firm* — Canon U.S.A., Inc. IP Division

(57) ABSTRACT

A measurement apparatus used for a sorting apparatus for sorting objects includes a scanning unit configured to perform scanning with illumination light which illuminates the object, a control unit configured to control the scanning unit, and a sensor configured to measure reflection light from the illuminated object, wherein the control unit controls the scanning unit to track the object with the illumination light by changing a position of the illumination light in a moving direction of the object and a direction perpendicular to the moving direction.

18 Claims, 6 Drawing Sheets

(56) References Cited

U.S. PATENT DOCUMENTS

| | | | | |
|---|---|---|---|---|
| 5,873,470 | A * | 2/1999 | Davis | B07C 5/366 |
| | | | | 209/555 |
| 5,936,229 | A * | 8/1999 | Livingston | F41H 13/005 |
| | | | | 250/203.2 |
| 6,060,677 | A * | 5/2000 | Ulrichsen | B07C 5/368 |
| | | | | 250/225 |
| 6,313,423 | B1 * | 11/2001 | Sommer | B07C 5/366 |
| | | | | 209/579 |
| 6,509,537 | B1 * | 1/2003 | Krieg | G01N 21/274 |
| | | | | 209/579 |
| 7,816,616 | B2 * | 10/2010 | Kenny | B07C 5/342 |
| | | | | 356/402 |
| 8,083,066 | B2 * | 12/2011 | Bourely | B07C 5/34 |
| | | | | 209/939 |
| 2011/0317001 | A1 * | 12/2011 | Massen | B07C 5/3425 |
| | | | | 348/91 |
| 2013/0056398 | A1 * | 3/2013 | Adams | B07C 5/342 |
| | | | | 209/587 |
| 2014/0203177 | A1 * | 7/2014 | Kinugawa | G01N 21/3563 |
| | | | | 250/339.11 |
| 2016/0252461 | A1 * | 9/2016 | Balthasar | G01N 21/85 |
| | | | | 356/445 |
| 2016/0354809 | A1 * | 12/2016 | Gruna | B07C 5/10 |
| 2019/0299255 | A1 * | 10/2019 | Chaganti | G06V 10/56 |
| 2020/0141865 | A1 * | 5/2020 | Hamada | G01N 21/359 |
| 2020/0300704 | A1 * | 9/2020 | Sekine | G01J 3/0208 |
| 2021/0346916 | A1 * | 11/2021 | Kumar | B07C 5/34 |
| 2021/0404947 | A1 * | 12/2021 | Ichihara | G01N 21/65 |
| 2022/0034800 | A1 * | 2/2022 | Kawaguchi | B07C 5/3427 |

FOREIGN PATENT DOCUMENTS

| | | | | |
|---|---|---|---|---|
| EP | 3896602 A1 * | 10/2021 | | B07C 5/342 |
| JP | 2009092458 A * | 4/2009 | | |
| JP | 2013036971 A * | 2/2013 | | |
| JP | 2014070903 A * | 4/2014 | | |
| JP | 2021527826 A | 10/2021 | | |
| KR | 20130023115 A * | 3/2013 | | |
| WO | WO-2021161779 A1 * | 8/2021 | | |

OTHER PUBLICATIONS

Aurelie Dupont, et al. "Nanoscale three-dimensional single particle tracking", Nanoscale, vol. 3, Aug. 2011, pp. 4532-4541.

* cited by examiner

SORTING APPARATUS FOR SORTING OBJECTS AND MEASUREMENT APPARATUS

BACKGROUND OF THE INVENTION

Field of the Invention

The present invention relates to a sorting apparatus for sorting objects and a measurement apparatus.

Description of the Related Art

Conventionally, from the perspective of mass-productivity and component cost, molded resinous components have been widely used for structural components and exterior components of automobiles and electric appliances. The recent industrial world is facing an urgent need to give consideration to the environment, so that these molded resinous components are recycled and reused. In the conventional recycling, waste automobiles and waste home electronics are crushed to a size of 10 to 100 mm and collected as residual substances containing various types of plastics after the substances such as iron and aluminum are collected in the course of various types of recycling processing.

In many cases, these residual substances are eventually reused as the fuel burned through thermal recycling processing.

An attempt to conduct horizontal recycling where these residual substances such as plastic are reused as the materials of molded resinous components has been made, and a resin identification apparatus for identifying and sorting a particular type of plastic from various residual substances containing plastic has been developed.

As a measurement method for specifying a resin type in a non-contact state by emitting light, the following technique which specifies a resin type by using the Raman scattering has been discussed.

A resin identification apparatus discussed in Japanese Patent Application Laid-Open No. 2013-36971 moves illumination light parallel to a conveyer-belt when resin conveyed by the conveyer-belt is measured by the Raman spectroscopy, so that a strong Raman scattering signal can be acquired without damaging or denaturalizing the resin. While emission of the excitation laser light is being performed, the resin identification apparatus moves a lighting optical system parallel to an upper face of a placement table in a range greater than or equal to a spot diameter of the excitation laser light on the target object, or preferably, in a range greater than or equal to two to three times the spot diameter. In this way, the excitation laser light is not intensively emitted to one point of the target object, so that the resin identification apparatus can prevent the target object from being damaged or denaturalized.

According to the technique discussed in Japanese Patent Application Laid-Open No. 2013-36971, even when high-power laser is emitted to the resin, a resin type can be identified through the Raman measurement without denaturalizing the resin. Generally, it is necessary to measure an extremely faint signal through the Raman measurement. Therefore, the identification apparatus has to include a laser light source having a high-output power. However, when use of a low-cost mountable laser diode (LD) as a light source is considered, it is necessary to improve a signal-noise (S/N) ratio because there is a limit to the output power of the LD. In order to acquire a Raman signal of high S/N ratio, for example, when measurement is performed, signal intensity is increased by extending the exposure time spent at the sensor by reducing the belt speed, and noise is reduced through repetitive averaging.

On the other hand, throughput of the identification processing has to be enhanced because a huge amount of residual resinous substances of 1 t/h to 2 t/h are generated in the course of the recycling processing. Therefore, it is desirable to increase the speed of the conveyer-belt. If a speed of the conveyer-belt is increased in order to enhance the throughput, a period of time the sample exists just beneath the illumination light is shortened, so that the exposure time necessary to perform Raman measurement through the spectroscope cannot be ensured, and the number of times of repetitive averaging cannot be ensured. Therefore, it is difficult to ensure the S/N ratio.

As described above, there is an issue that sorting of resin cannot easily be executed while achieving both of the high S/N ratio and the high throughput.

SUMMARY OF THE INVENTION

According to an aspect of the present invention, a measurement apparatus used for a sorting apparatus for sorting objects includes a scanning unit configured to perform scanning with illumination light which illuminates the object, a control unit configured to control the scanning unit, and a sensor configured to measure reflection light from the illuminated object, wherein the control unit controls the scanning unit to track the object with the illumination light by changing a position of the illumination light in a moving direction of the object and a direction perpendicular to the moving direction.

Further features of the present invention will become apparent from the following description of exemplary embodiments with reference to the attached drawings.

DESCRIPTION OF THE EMBODIMENTS

The exemplary embodiment of the present invention will be described in detail with reference to the appended drawings.

Figure 1:
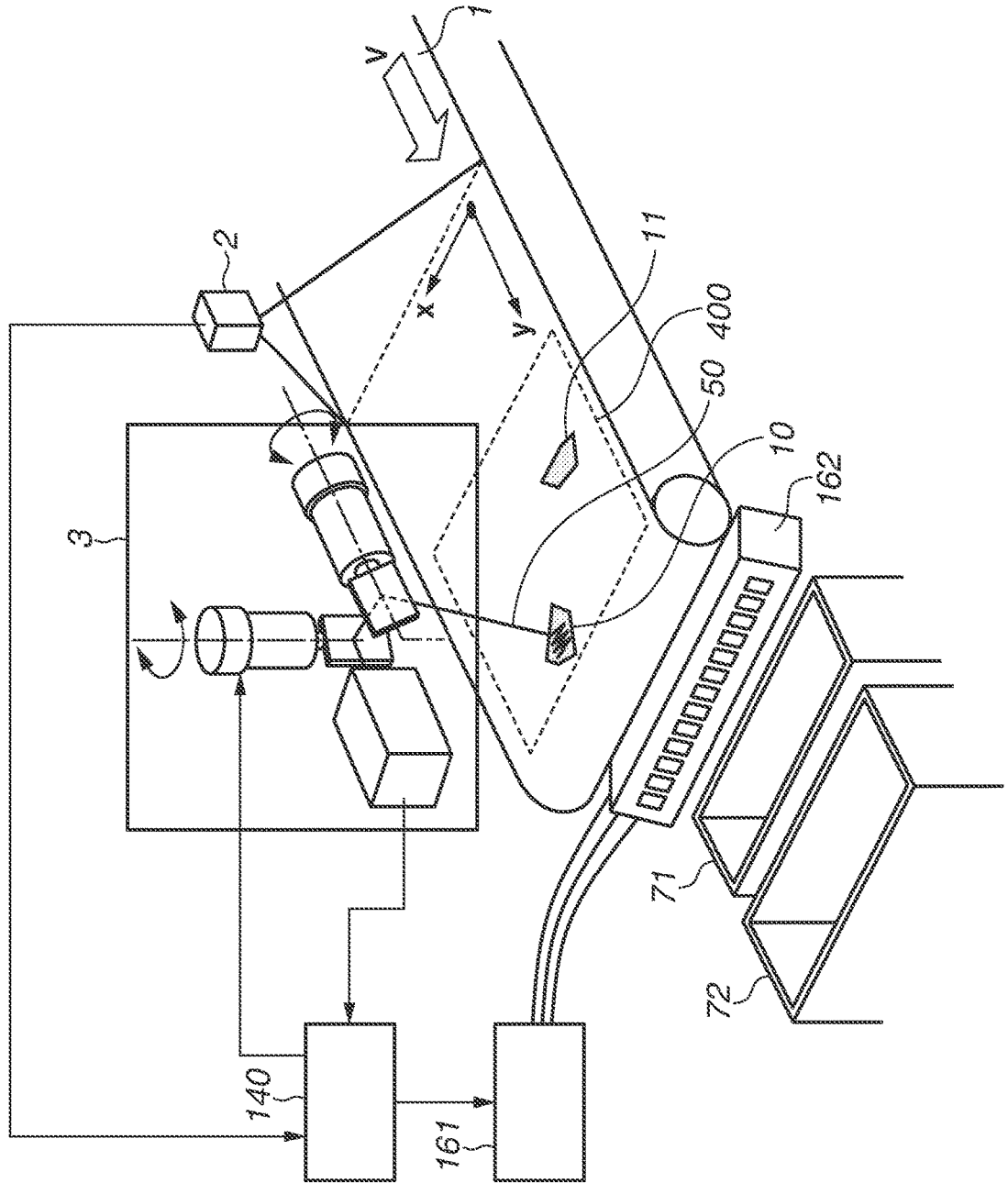
FIG. 1 is a diagram illustrating a sorting system.

FIG. 1 is a diagram illustrating a configuration of a sorting system. The sorting system according to the present exemplary embodiment includes a conveyer-belt 1 (moving unit) for conveying a sample (object). The sorting system is a system which executes identification processing for identifying a type of a sample conveyed by the conveyer-belt 1 and sorts out a sample based on an identification result thereof.

Samples 10 and 11 are objects such as a piece of metal mainly containing metal, a piece of ceramic mainly containing metallic oxide crystals, a piece of glass mainly containing non-crystalline metallic oxides, and a piece of resin mainly containing resin. In many cases, the samples 10 and 11 are industrial waste such as discarded home electronics and waste automobiles, crushed to flat pieces having sizes of approximately 10 to 100 mm by crushing processing performed as the preprocessing of recycling processing.

In the present specification, "resin" generally refers to a polymer of organic materials including thermoplastic resin (plastic), thermosetting resin, rubber, elastomer, cellulose, and paper.

In addition, the samples 10 and 11 may contain various additive substances such as glass filler, fiber filler, a flame retardant, and a plasticizing agent.

The sorting system according to the present exemplary embodiment identifies not only a type of resin which constitutes a piece or resin, i.e., a type (material and color) of a piece of resin, but also presence or absence of the above-described additive substances and the type thereof.

In the sorting system according to the present exemplary embodiment, samples to be sorted are fed to the conveyer-belt 1 by a quantitative delivery device and a vibrating feeder (not illustrated) and conveyed on the conveyer-belt 1. A recognition unit (measuring unit) 2, a measurement unit 3, and a sorting unit 162 are arranged on the conveyer-belt 1 in that order from an upstream side of the moving direction of the conveyer-belt 1, and the sample 10 that has passed the lower side of the recognition unit 2 and the measurement unit 3 is dropped from the conveyer-belt 1 and passes across the front face of the sorting unit 162.

The recognition unit 2 executes image processing of a two-dimensional image including a sample captured by an area scan camera capable of collectively capturing a two-dimensional image or a line scan camera capable of reconstructing a two-dimensional image. For example, the recognition unit 2 calculates a coordinate p1(x1, y1) of a position where the sample 10 exists at a time to based on a result of the image processing and the information about a shape and a size of the sample 10.

Figure 3:
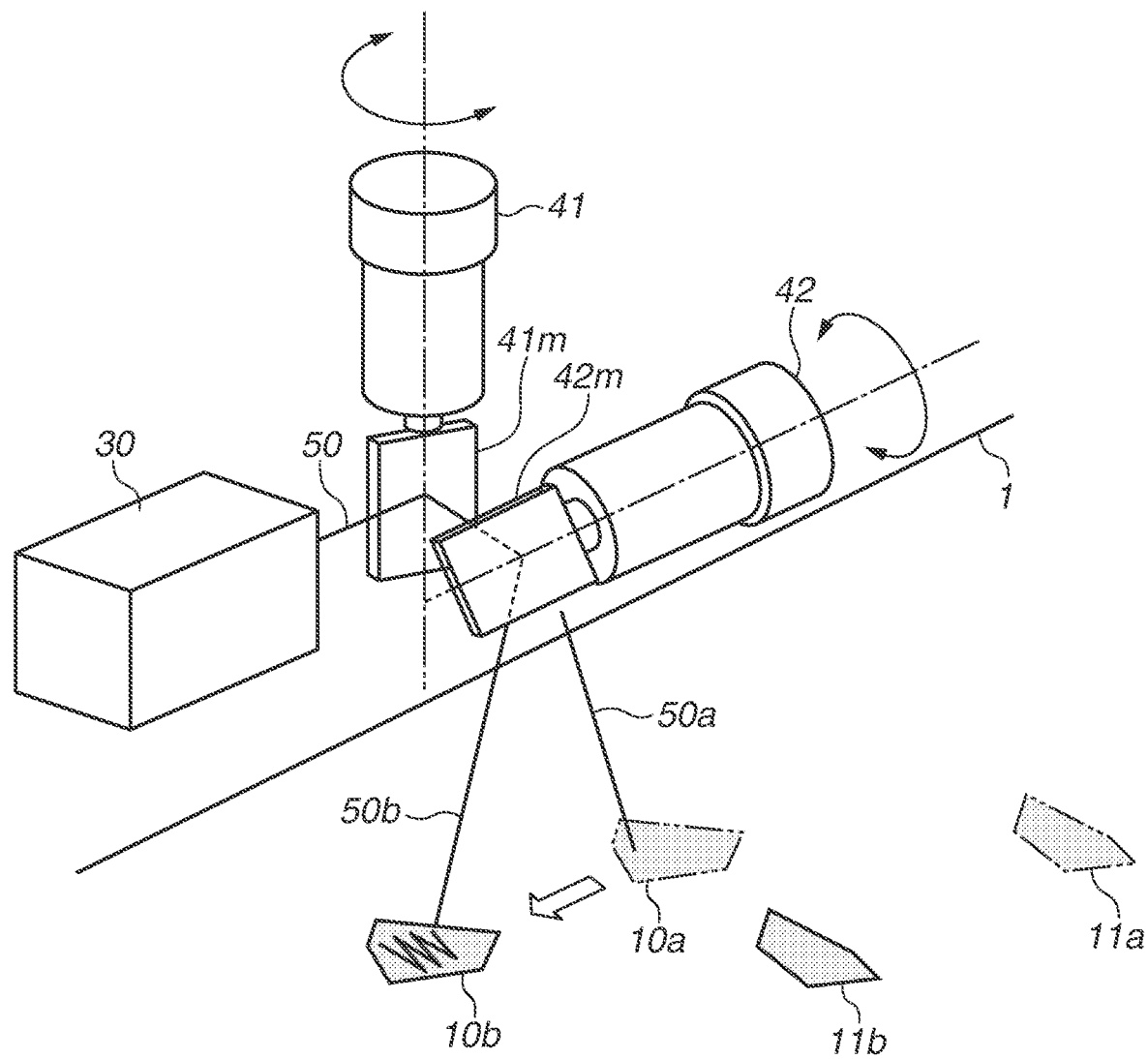
FIG. 3 is a diagram illustrating a state where galvano scanners perform scanning with illumination light.

As illustrated in FIG. 3, the measurement unit 3 includes galvano scanners 41 and 42 (scanning unit) for performing scanning with illumination light 50, and an optical spectroscopic unit 30 for measuring Raman scattering light (reflection light) from a sample. The measurement unit 3 controls the scanning unit to incline the illumination light 50 at an angle as expressed by illumination light 50a or 50b by inclining a principal light ray of the illumination light 50, using the measurement unit 3 as a reference, and brings the illumination light (measurement point) into a movable state.

Figure 2:
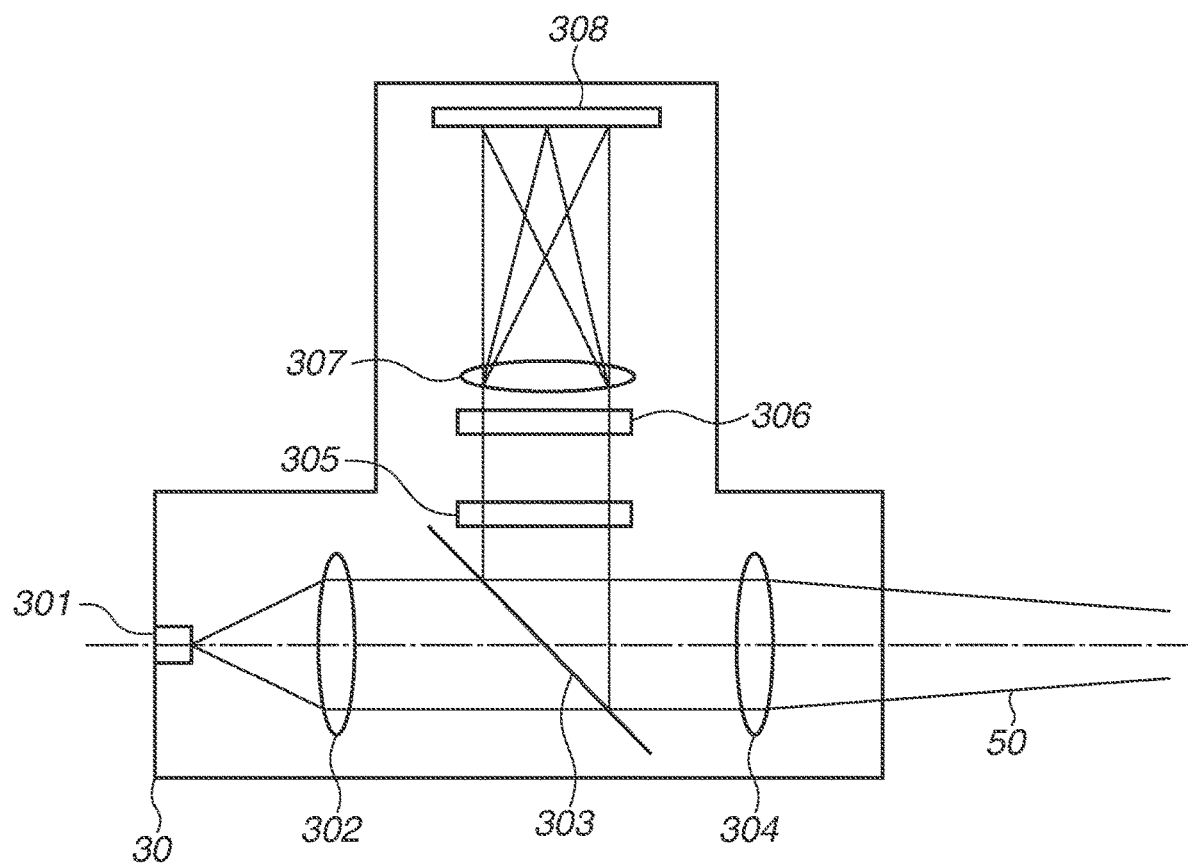
FIG. 2 is a diagram illustrating details of a measurement unit.

As illustrated in FIG. 2, the optical spectroscopic unit 30 includes a light source 301 and a lens (illumination unit) 302.

The optical spectroscopic unit 30 irradiates mirrors included in the galvano scanners 41 and 42 with laser light as the illumination light 50 from the light source 301 via lenses 302 and 304. A dichroic mirror 303 is arranged at a position between the lenses 302 and 304, and transmits light of a wavelength λ from the light source 301.

A processing unit 140 includes a control unit for controlling the galvano scanners 41 and 42. The processing unit 140 calculates a position coordinate p1(x1, y1+V(t1−t0)) of a moving sample at a time t1 from a speed V of the conveyer-belt 1 adjusted or measured previously and a time to at which the sample is recognized by the recognition unit 2. Then, at a time when the sample 10 reaches the scanning area 400 the galvano scanners 41 and 42 can scan with the illumination light 50, the processing unit 140 outputs control instructions to the galvano scanners 41 and 42 to control the galvano scanners 41 and 42 to illuminate the sample 10 with the illumination light 50. Then, the processing unit 140 controls the galvano scanners 41 and 42 to track the moving sample 10 with the illumination light 50. By using the two galvano scanners 41 and 42, scanning can be performed with illumination light 50 in the y axis direction, i.e., a moving direction of the conveyer-belt 1 (sample 10) and an x axis direction perpendicular to the y axis direction.

Figure 4:
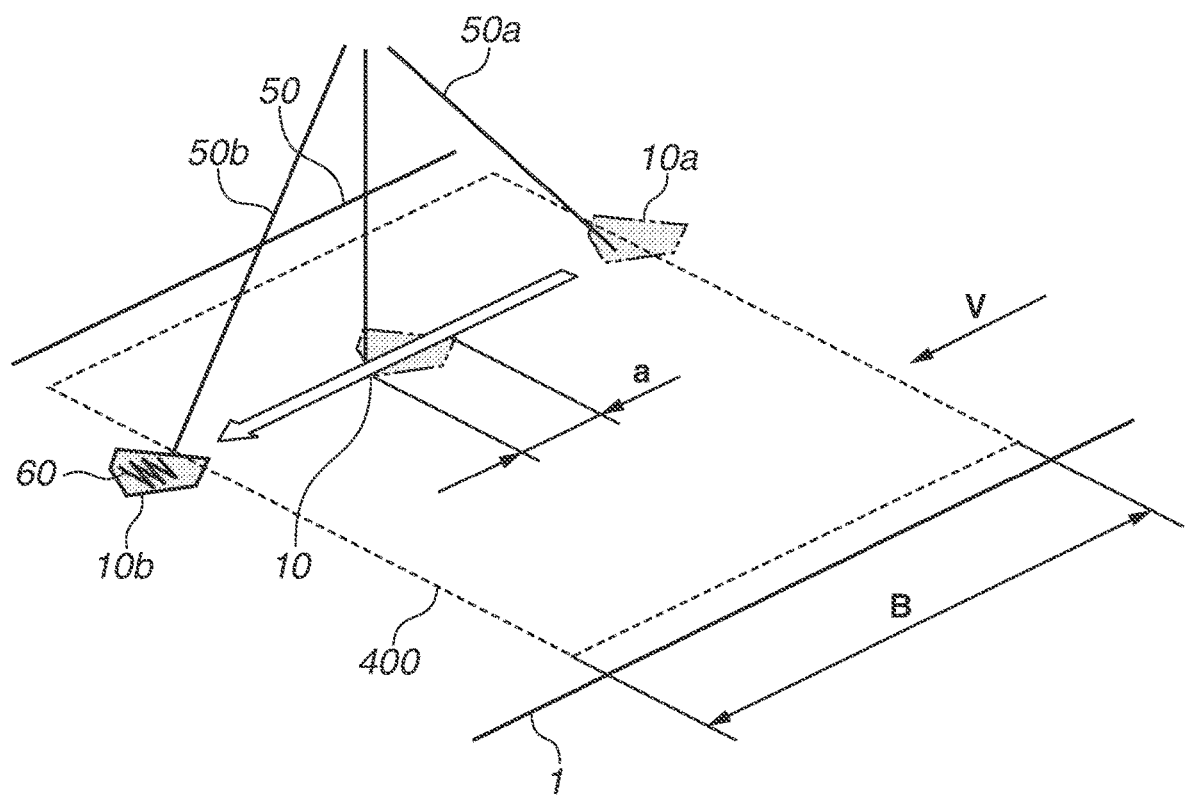
FIG. 4 is a diagram illustrating a state where a scanning area is scanned with illumination light.

Specifically, as illustrated in FIG. 4, at a time point (position 10a) when the sample 10 reaches a boundary of the scanning area 400 on the upstream side in the moving direction of the conveyer-belt 1, the measurement unit 3 performs scanning with the illumination light 50 at a position of the illumination light 50a to start the measurement. The measurement unit 3 draws a locus 60 on the sample 10 to illuminate the sample 10 to perform the Raman measurement while the sample 10 moves at a speed V according to the movement of the conveyer-belt 1. Then, the measurement unit 3 completes the measurement when the sample 10 reaches a boundary (position 10b) of the scanning area 400 on the downstream side of the conveyer-belt 1. Herein, a locus from the illumination light 50a to the illumination light 50b expresses an average position of the illumination light 50 when scanning is performed.

A length of the scanning area 400 in a belt moving direction is expressed as "B". A position of the illumination light 50 changes in a direction the same as the belt moving direction, and the illumination light 50 illuminates the sample 10 for a time T (T=B/V) while tracking the sample 10 without staying at one point on a surface of the sample 10.

Therefore, energy of the illumination light 50 does not concentrate on one point of the sample 10, so that the measurement unit 3 can perform the Raman measurement without denaturalizing the resin. Further, because the conveyer-belt 1 can be operated at high speed, even if a huge amount of samples are fed to the conveyer-belt 1 for the sake of enhancing the throughput of identification, the samples can be arranged in a spatially separated state.

In the conventional method in which the illumination light 50 does not perform scanning, the sample 10 is irradiated for a time t (t=a/V) when a size of the sample 10 in the belt moving direction is "a".

The present exemplary embodiment will be described with respect to a case where a speed of the conveyer-belt 1 is 1 m/s, a size of the sample 10 assumed to be a minimum size in the recycling processing is 10 mm, and a scanning area B is set as 200 mm.

In the conventional method in which illumination light is fixed, the time t the sample can be illuminated with illumination light is 10 ms. On the other hand, in the method in which the measurement is executed while the sample is being tracked and scanned with the illumination light 50, measurement can be executed for approximately 200 ms. Therefore, with respect to black resin whose reflection light amount is small, a signal-noise ratio (S/N) of a faint Raman signal can be improved by extending the exposure time, or by averaging the data acquired by executing measurement for the exposure time of 10 ms twenty times.

On the other hand, in the present exemplary embodiment, while the sample 10 is being measured, the illumination light 50 draws a zigzag locus, such as a locus 60, without staying at one place. Therefore, energy of the illumination light 50 is widely dispersed in the area of the sample 10, so that the resin is not denaturalized while measurement is being executed.

As described above, the illumination light 50 from the optical spectroscopic unit 30 is reflected on the mirror portions 41m and 42m of the galvano scanners 41 and 42 and irradiate the sample 10.

After the illumination light 50 is reflected on the sample 10, Raman scattering light is reflected isotropically, reflected on the mirror portions 41m and 42m of the galvano scanners 41 and 42 again, and returns to the optical spectroscopic unit 30. The Raman scattering light is Raman-shifted depending on the substances of the material of the sample 10. Therefore, the Raman scattering light is subsequently reflected on the dichroic mirror 303, and only the components thereof which have been Raman-shifted are transmitted through a bandpass filter 305 serving as an excitation light cut filter and dispersed by a spectroscopic element 306 (spectroscopic unit). The light flux dispersed by the spectroscopic element 306, diffracted by a diffraction angle different for each wavelength, is condensed again through a lens 307, and Raman-shifted light of each wavelength is received by a light receiving element arranged on the sensor array 308. A signal output from the light receiving element is transmitted to the processing unit 140 as a characteristic signal depending on the substance of the sample. Then, for example, the processing unit 140 compares a waveform thereof with a unique waveform of a known material previously acquired by measuring a sample of the known material to specify the material, and identifies a type of the sample.

For example, a signal (measurement result) from the sensor array 308 is transmitted to the processing unit 140 at 300 fps. The measurement is started at a time point when the sample 10 reaches the position 10a, i.e., a boundary of the scanning area 400 on the upstream side in the belt moving direction. Then, the processing unit 140 extracts a signal corresponding to that measurement from a group of signals transmitted from the sensor array 308 at 300 fps and specifies a material. For example, a corresponding signal may be determined and extracted based on a time the operation instruction is issued.

In a case where the processing unit 140 identifies the type of the sample 10 and determines that the sample 10 is a sorting target material, an opening signal is transmitted to the sorting unit 162 via the sorting controller 161 at a time t2 when the sample 10 passes the sorting unit 162. Then, air is spouted from a portion of the sorting unit 162 at a position corresponding to a coordinate x1 of the sample 10 measured by the recognition unit 2, so that the sample 10 is blown off by the air and collected to a collection box 72. In a case where the sample 10 is not a sorting target, the sample 10 is thrown out and dropped from the conveyer-belt 1 at a speed V and collected to a collection box 71.

After measurement of the sample 10 is completed, the measurement unit 3 executes measurement of the sample 11 and subsequent samples (not illustrated) which are continuously fed and conveyed thereto. The measurement unit 3 turns the galvano scanners 41 and 42 to change the inclination angle of the illumination light 50 to move the illumination light 50 to a starting point for executing measurement of the sample 11. Because the galvano scanners 41 and 42 can rapidly perform scanning with the illumination light 50, a moving time until measuring the next resin can be shortened. Therefore, the galvano scanners 41 and 42 can continuously measure the samples conveyed one after another. As a result, the number of samples measured by the Raman measurement with long measurement time and high S/N ratio is increased, so that resin can be sorted with high throughput.

In the present exemplary embodiment, the recognition unit 2 acquires a two-dimensional image captured by an area sensor or a line sensor, and calculates a coordinate of a sample through the image processing. However, the configuration is not limited thereto. For example, an object may be recognized based on the height information acquired by a light-sectioning sensor. Further, in the present exemplary embodiment, a zigzag locus has been described as a locus which the illumination light 50 draws on resin without stopping at one point thereof. However, it is obvious that the same effect can be acquired as long as the illumination light 50 does not stop at one point on resin. For example, the illumination light 50 may continuously make a circular or helical motion, or may draw a square-shape locus.

Further, according to the configuration described in the present exemplary embodiment, the recognition unit 2 acquires a two-dimensional image which includes a sample. This two-dimensional image includes brightness of the sample, i.e., information about diffuse reflectivity. According to the study conducted by those skilled in the art, it was found that light intensity of the Raman scattering correlates with diffuse reflectivity, and that intensity of the Raman scattering light coming from a white sample having high brightness is much higher than the Raman scattering light coming from a black sample having low brightness. In other words, a measurement time of the white sample necessary to acquire the same S/N ratio can be shorter than that of the black sample.

Figure 5:
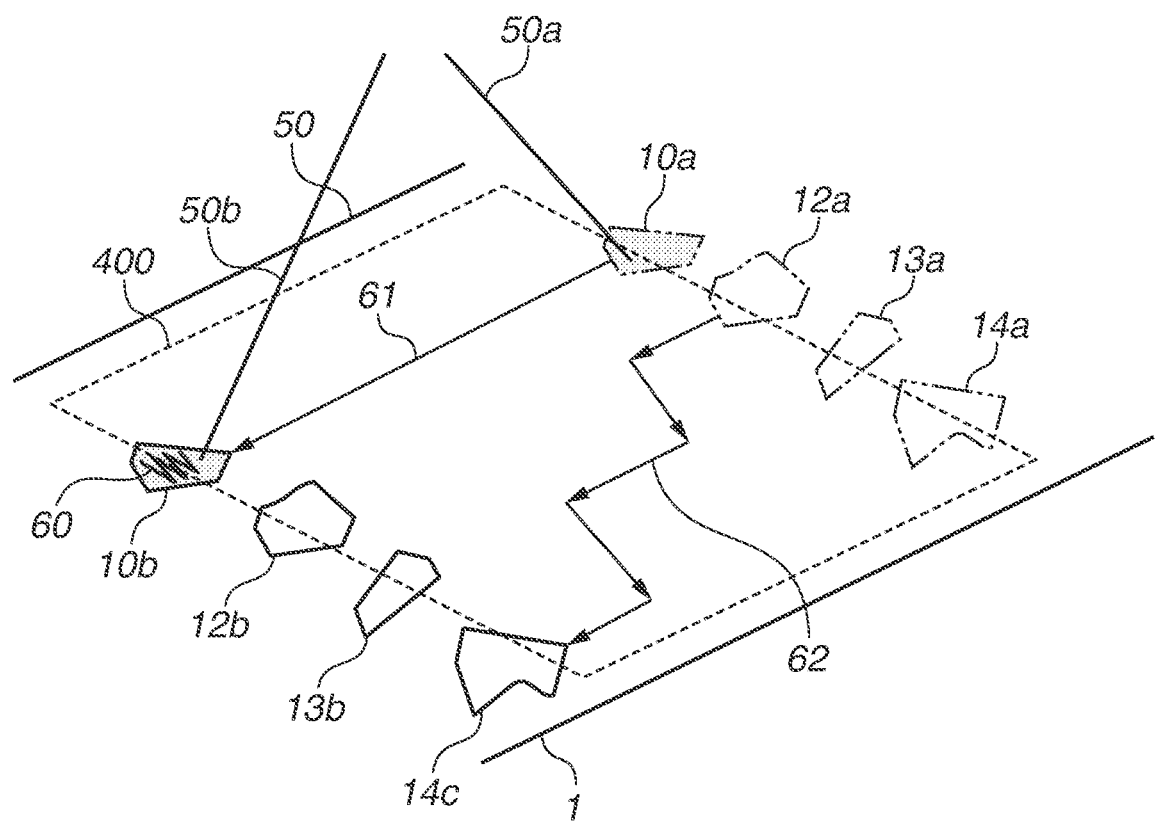
FIG. 5 is a diagram illustrating a scanning locus drawn when a plurality of samples is measured in a scanning area.

In view of the above-described fact, in order to efficiently execute identification of the sample for the sake of improving the throughput, it is effective to make the measurement time of the white resin be shorter than the measurement time of the black resin. In this case, as illustrated in FIG. 5, with respect to the sample 10 which is black resin, the galvano scanners 41 and 42 perform scanning with the illumination light 50 under the scanning condition that measurement is executed along a locus 61 which is drawn across the entire scanning area 400 from the position 10a to the position 10b.

On the other hand, with respect to the white resin, for example, scanning is performed with illumination light 50 under the scanning condition that measurement is executed in a measurement time one-third the measurement time of the black resin. For example, scanning is performed with the illumination light 50 along a step-like locus 62. In this way, with respect to samples 12, 13, 14 having high brightness, conveyed side by side from a position 12a to a position 12b, a position 13a to a position 13b, and a position 14a to a position 14b, the measurement unit 3 can measure all of these three samples 12, 13, and 14. In this case, the loci 61 and 62 illustrate the average positions of the illumination light 50 when scanning is performed, and it is needless to say that the illumination light 50 simultaneously draws the locus 60 on the resin while the average positions thereof are being moved on the respective loci 61 and 62. As described above, the processing unit 140 includes a control unit which controls the scanning unit to change the scanning condition of illumination light 50 based on the information about the object.

In addition, samples conveyed thereto are different in size and color. As described above, the higher the brightness of the sample is, the higher the Raman scattering intensity becomes, and the lower the brightness of the sample is, the lower the Raman scattering intensity becomes. Therefore, the higher the brightness is, the higher the identification reliability of the specified resin type, and the lower the brightness is, the lower the identification reliability of the specified resin type. It is obvious that a utility value of a desired type of collected resin is increased when its purity is high. Further, it is preferable that resin having higher brightness be collected preferentially because the identification reliability is improved, and purity of a desired type of collected resin is increased as well.

On the other hand, the samples existing in the scanning area 400 are actually conveyed by the conveyer-belt 1 in a random arrangement. Therefore, there is a possibility that the samples exist in high distribution density. In such a case, there is not enough time to sequentially scan and measure the entire group of resin in high distribution density with the illumination light 50. In this case, the processing unit 140 may instruct the galvano scanners 41 and 42 to skip the measurement of some samples. In other words, in a case where a plurality of objects exists in an area scannable with the illumination light 50, the processing unit 140 determines a measurement target object based on the information about the object.

At this time, the samples having high brightness are measured preferentially based on the information about brightness of respective samples captured in the image acquired by the recognition unit 2. In this way, it is possible to improve the purity of collected samples. Further, it is also effective to increase the amount of collected resin in the end by preferentially measuring the samples having large size, based on the information about a shape of the sample acquired by the recognition unit 2.

According to the configuration described in the present exemplary embodiment, the processing unit 140 sets the previously adjusted or measured speed V as a speed of the conveyer-belt 1 and issues an instruction for causing the measurement unit 3 to track the sample with the illumination light 50 and an instruction for causing the sorting unit 162 to perform the sorting operation based on time. However, for example, measuring devices such as a laser Doppler velocimeter and an image correlation displacement meter, which directly measure a speed of the conveyer-belt 1, may be arranged in the peripheries of the recognition unit 2 and the measurement unit 3, so that the processing unit 140 can receive the measurement values relating to the belt moving amount from these measuring devices. With this configuration, the processing unit 140 can issue the operation instructions to the galvano scanners 41 and 42 based on the belt moving amount measured thereby. It is effective to perform the tracking operation with the illumination light 50 more precisely and to perform sorting operation by the sorting unit 162 more precisely to increase the collection amount. In this case, as a method for extracting a signal generated at a time when a sample is illuminated, from a group of signals transmitted from the sensor array 308, the processing unit 140 can determine the signal by using a measurement value relating to the belt moving amount acquired when each signal is generated. In this way, the processing unit 140 can precisely extract a signal generated when the illumination light 50 exists on the resin.

Figure 6:
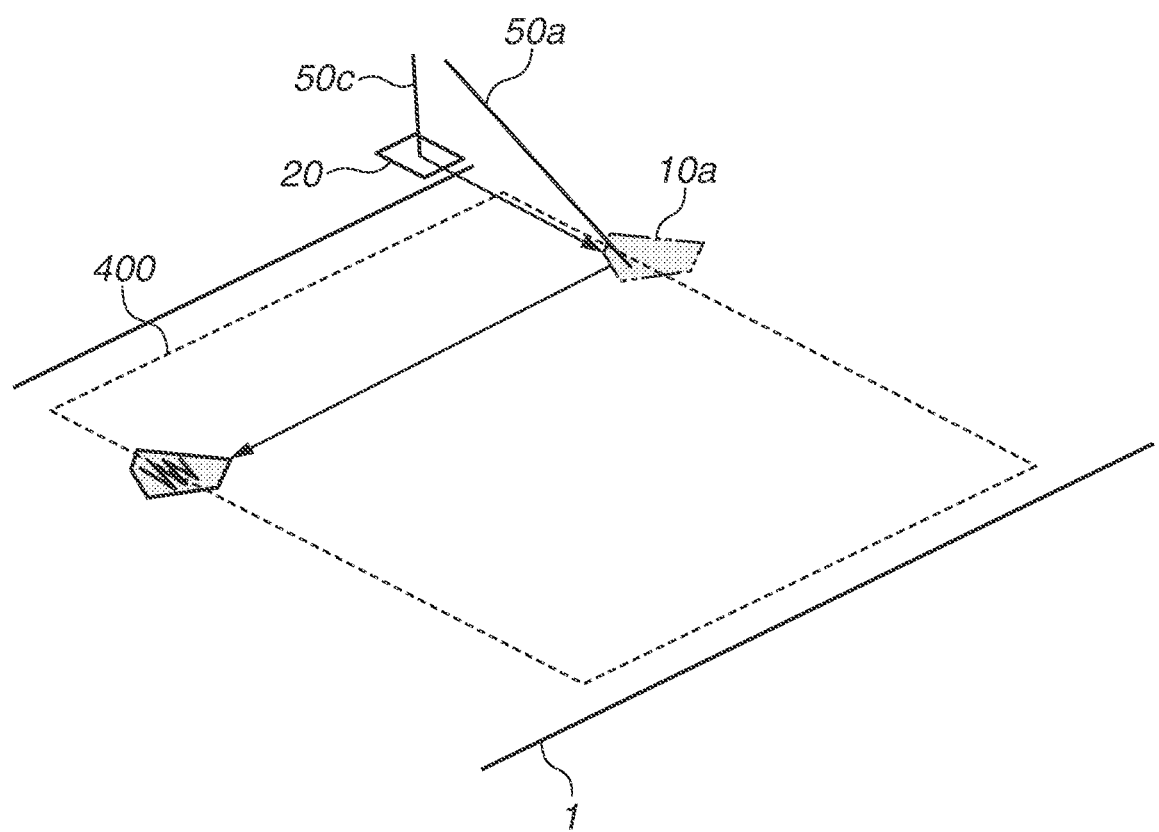
FIG. 6 is a diagram illustrating a state where a sample arranged outside the scanning area is measured.

With respect to extraction of the signal, it is also effective to measure a sample which exhibits a known specific characteristic (feature) not assumed in the normal measurement in advance, prior to the specified time or immediately before the illumination light 50 moves to the measurement starting point. For example, a sample having high reflectivity, whose measurement value is saturated, may be measured previously. For example, as illustrated in FIG. 6, a fluorescent sample 20 having high fluorescence, whose measurement value is saturated at the sensor array 308, is arranged at a position outside the scanning area 400 and where the measurement unit 3 can perform measurement. Then, prior to the specified time or immediately before the sample 10 that has reached the position 10a on the border of the scanning area 400 on the upstream side in the belt moving direction is scanned with the illumination light 50, the measurement unit 3 illuminates the fluorescent sample 20 by changing the angle of the illumination light 50 to an angle expressed by an illumination light 50c and measures the fluorescent sample 20. In this way, in the subsequent stage, the processing unit 140 can easily extract the measurement data. As the data to be used for determining a material of the sample, the processing unit 140 may extract, from the data continuously transferred from the sensor array 308, data transferred immediately after data indicating the element having a maximum signal value or data transferred after the specified number of pieces of data, and executes the processing.

The sample which indicates the characteristic data is not limited to the above, and any sample which exhibits a known specific characteristic, not assumed in the normal measurement, can be used. For example, the sample may be a light trap having an extremely small amount of reflection light, or resin alloy which simultaneously exhibits characteristics of a plurality of types of resin.

As described above, based on the information about the resin recognized by the recognition unit 2, the galvano scanners 41 and 42 described as an example of the scanning unit makes the average positions follow the belt moving direction to illuminate the sample with the illumination light 50 by changing the principal light ray angle of the illumination light 50. Further, while the measurement is being executed, even if the belt speed is high, the measurement unit 3 tracks the sample to execute point-measurement through the Raman spectroscopy by performing scanning with the illumination light 50 without making the illumination light 50 stay at the same position on the resin. Therefore, the measurement unit 3 can identify the resin through the Raman spectroscopy while achieving both of the high S/N and the high throughput.

According to the present exemplary embodiment, it is possible to provide an identification apparatus capable of achieving both of the high S/N ratio and the high throughput.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2022-078799, filed May 12, 2022, which is hereby incorporated by reference herein in its entirety.

What is claimed is:

1. A measurement apparatus comprising:
    a scanning unit configured to move illumination light to illuminate an object configured to move;
    a control unit configured to control the scanning unit; and
    a sensor configured to measure reflection light from the illuminated object,
    wherein the control unit controls the scanning unit so that the illumination light from the scanning unit to illuminate the object tracks the moving object, and
    wherein the sensor includes a spectroscopic unit configured to disperse scattering light from the object illuminated by the illumination light.

2. The measurement apparatus according to claim 1, wherein the control unit controls the scanning unit to prevent the illumination light from staying at one point on a surface of the object while the moving object is being measured.

3. The measurement apparatus according to claim 1, wherein the scanning unit performs scanning with the illumination light in a direction perpendicular to a moving direction of the object while performing scanning with the illumination light in the moving direction of the object.

4. The measurement apparatus according to claim 1, wherein the control unit controls the scanning unit to change a scanning condition of the illumination light based on information about the object.

5. The measurement apparatus according to claim 1, wherein, in a case where a plurality of objects exists in an area scannable with the illumination light, the control unit determines a measurement target object based on information about the object.

6. The measurement apparatus according to claim 5, wherein the information about the object includes brightness or size of the measured reflection light from the illuminated object.

7. The measurement apparatus according to claim 1, wherein the measurement apparatus identifies a type of the object by using data previously obtained by measuring samples by the sensor.

8. The measurement apparatus according to claim 1, further comprising a measurement unit configured to measure a position or a speed of the moving object,
wherein the control unit controls the scanning unit based on the object position or the object speed measured by the measurement unit while the object is being illuminated by an illumination light.

9. The measurement apparatus according to claim 1, wherein the measurement apparatus is configured to identify a type of resin as the object.

10. The measurement apparatus according to claim 1, wherein the scanning unit includes a galvano scanner.

11. The measurement apparatus according to claim 1, wherein the control unit controls the scanning unit based on a position of the object to make the scanning unit track the moving object with the illumination light and change a position of the illumination light on a surface of the object.

12. The measurement apparatus according to claim 1, further comprising a recognition unit configured to recognize a position of an object,
wherein, based on a position of the object obtained from the recognition unit, the control unit makes the scanning unit perform scanning with the illumination light.

13. A sorting apparatus for sorting an object, the sorting apparatus comprising:
a measurement apparatus; and
a sorting unit configured to sort the object based on a measurement result obtained by the measurement apparatus,
wherein the measurement apparatus includes:
a scanning unit configured to move illumination light to illuminate an object configured to move,
a control unit configured to control the scanning unit, and
a sensor configured to measure reflection light from the illuminated object,
wherein the control unit controls the scanning unit so that the illumination light from the scanning unit to illuminate the object tracks the moving object.

14. The sorting apparatus according to claim 13, further comprising a moving unit configured to move the object.

15. The measurement apparatus according to claim 1, wherein, in tracking the moving object, the illumination light that illuminates the object moves in accordance with the movement of the object in a direction of movement of the moving object.

16. The measurement apparatus according to claim 1, wherein the control unit controls the scanning unit so that the illumination light from the scanning unit to illuminate the object tracks the moving object, and a position of the illumination light that illuminates the object is moved in two directions that are perpendicular to each other.

17. The measurement apparatus according to claim 16, wherein the scanning unit includes a plurality of galvano scanners configured to move the position of the illumination light in the two directions that are perpendicular to each other.

18. The measurement apparatus according to claim 16, wherein, in moving the position of the illumination light when the object to be moved is illuminated, the illumination light does not deviate from the object.

* * * * *